US011247032B1

(12) United States Patent
Knas et al.

(10) Patent No.: US 11,247,032 B1
(45) Date of Patent: Feb. 15, 2022

(54) WEARABLE BAND FOR TRANSDERMAL DRUG DELIVERY

(71) Applicant: MASSACHUSETTS MUTUAL LIFE INSURANCE COMPANY, Springfield, MA (US)

(72) Inventors: Michal Knas, Monson, MA (US); Jiby John, Suffield, CT (US)

(73) Assignee: MASSACHUSETTS MUTUAL LIFE INSURANCE COMPANY, Springfield, MA (US)

(*) Notice: Subject to any disclaimer, the term of this patent is extended or adjusted under 35 U.S.C. 154(b) by 628 days.

(21) Appl. No.: 16/125,056

(22) Filed: Sep. 7, 2018

Related U.S. Application Data

(60) Provisional application No. 62/555,296, filed on Sep. 7, 2017.

(51) Int. Cl.
*A61M 37/00* (2006.01)
(52) U.S. Cl.
CPC ..... *A61M 37/00* (2013.01); *A61M 2037/0007* (2013.01); *A61M 2205/502* (2013.01); *A61M 2209/088* (2013.01)
(58) Field of Classification Search
CPC .............. A61M 37/00; A61M 5/14244; A61M 5/14248; A61M 2005/14268; A61M 2005/3022
See application file for complete search history.

(56) References Cited

U.S. PATENT DOCUMENTS 4,549,879 A * 10/1985 Groshong ......... A61M 25/0075
604/247
4,710,167 A 12/1987 Lazorthes
(Continued)

FOREIGN PATENT DOCUMENTS

EP 2737891 A1 6/2014
WO 2009125398 A2 10/2009
(Continued)

OTHER PUBLICATIONS

Ahlam Zaid Alkilani et al, "Transdermal Drug Delivery: Innovative Pharmaceutical Developments Based on Disruption of the Barrier Properties of the stratum corneum", https://www.ncbi.nlm.nih.gov/pmc/articles/PMC4695828/>, Pharmaceutics; Oct. 22, 2015; 35 pages.
(Continued)

*Primary Examiner* — Kai H Weng
(74) *Attorney, Agent, or Firm* — Foley & Lardner LLP

(57) ABSTRACT

A wearable band transdermal medication device including one or more chamber for dispensing liquid transdermal medication, a device housing, and a transdermal applicator for the transdermal medication. The chamber includes a pouch containing a liquid transdermal medication pressurized at a first pressure, and an outlet for selective dispensing of the medication to a delivery section of the transdermal medication delivery device. The outlet may be a self-sealing membrane that dispenses liquid medication when subjected to a negative pressure differential, or may be a magnetic valve assembly. The device is configured as wristband, armband or other band worn by the patient with the transdermal applicator at an outer face of the device housing in contact with the patient's skin. A plurality of chambers housed by the device operate under electrical control to dispense medication, subject to access authorization, and subject to regimens for transdermal administration of the liquid medication.

14 Claims, 8 Drawing Sheets

(56) References Cited

U.S. PATENT DOCUMENTS

| | | | |
|---|---|---|---|
| 5,353,961 A | 10/1994 | Debush | |
| 6,110,152 A | 8/2000 | Kovelman | |
| 6,723,086 B2 | 4/2004 | Bassuk et al. | |
| 7,776,006 B2 | 8/2010 | Childers et al. | |
| 7,850,663 B2 | 12/2010 | Sullivan et al. | |
| 8,167,171 B2 | 5/2012 | Moretti | |
| 2002/0072733 A1* | 6/2002 | Flaherty | A61M 5/14248 604/890.1 |
| 2005/0000514 A1 | 1/2005 | Sullivan et al. | |
| 2008/0051716 A1* | 2/2008 | Stutz | G01F 11/06 604/151 |
| 2009/0012457 A1 | 1/2009 | Childers et al. | |
| 2009/0086579 A1 | 4/2009 | Clark | |
| 2011/0282282 A1* | 11/2011 | Lorenzen | A61M 5/14248 604/131 |
| 2011/0306941 A1* | 12/2011 | Chandrasekar | A61M 3/0254 604/262 |
| 2012/0041778 A1 | 2/2012 | Kraft | |
| 2016/0022539 A1 | 1/2016 | Daines | |
| 2016/0167864 A1* | 6/2016 | De Cleir | B65D 47/2018 206/221 |
| 2017/0035652 A1 | 2/2017 | Baker et al. | |

FOREIGN PATENT DOCUMENTS

| | | |
|---|---|---|
| WO | 2013142339 A1 | 9/2013 |
| WO | 2016083665 A1 | 6/2016 |
| WO | 2016102284 A1 | 6/2016 |
| WO | 2017007546 A1 | 1/2017 |

OTHER PUBLICATIONS

Thomas Rades et al., Pharmaceutics—Drug Delivery and Targeting, "Controlling drug delivery", Chapter I, Pharmaceutical Press; published Oct. 16, 2009; 24 pages.

"Philips Medication Dispensing Service", <https://www.slideshare.net/ferdlifeline/philips-medication-dispenser>; article downloaded May 3, 2017; 7 pages.

"Philips Lifeline Review", <http://medicalalertsystemshq.com/reviews/philips-lifeline-review.html>; article downloaded May 3, 2017; 7 pages.

"Smart Infusion Pumps", Greystone Research Associates, <https://greystoneassociates.org/wp.../12/Smart-Infusion-Pumps-Report-Brochure.pdf>, published Dec. 2016, 6 pages.

* cited by examiner

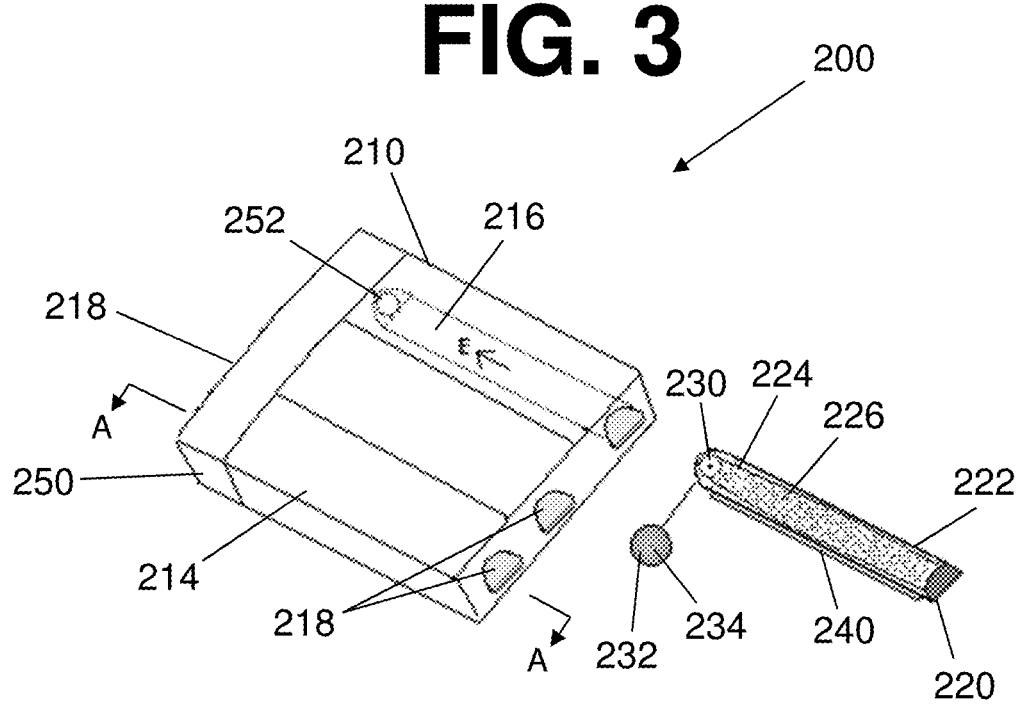

WEARABLE BAND FOR TRANSDERMAL DRUG DELIVERY

CROSS-REFERENCE TO RELATED APPLICATION

The present application claims benefit of U.S. Provisional Application No. 62/555,296 filed Sep. 7, 2017, entitled WEARABLE BAND FOR TRANSDERMAL DRUG DELIVERY, the entire contents of which are hereby incorporated by reference.

TECHNICAL FIELD

The present disclosure relates generally to mobile devices for transdermal drug delivery, and more particularly to wearable bands for personalized transdermal drug delivery.

BACKGROUND

Individuals with chronic or terminal medical conditions are frequently required to take many different medications on irregular schedules. Often these individuals are hospitalized in order to control the administration of the medications and for monitoring purposes. Even for those ambulatory individuals who are not hospitalized but require long-term medications, the administration of these medications poses various difficulties for the patient or other user. For example, these users may need to carry their medications with them at all times, to administer medications at inconvenient times and in awkward locations, or to stay home to follow their medication regime.

Transdermal drug delivery ("TDD") is a painless method of delivering drugs by applying a drug formulation onto intact and healthy skin. The drug initially penetrates through the stratum corneum and then passes through the deeper epidermis and dermis without drug accumulation in the dermal layer. A number of transdermal drug delivery systems are currently in use. Most TDD systems take the form of a drug patch containing the active constituent dispersed or suspended in a reservoir, with its rate of release controlled through passive administration by matrix diffusion or by passage through a controlling membrane. A drug patch is desirable for patient use because it is inconspicuous, easy to use, and allows the patient to be ambulatory while taking the medication.

A positive feature of transdermal drug delivery is improved patient compliance and acceptability of the drug therapy. TDD can improve patient compliance due to the reduction of dosing frequencies. TDD is also suitable for patients who are unconscious or vomiting, or persons who rely on self-administration. While transdermal administration is known to improve patient compliance, transdermal medication devices are typically designed for timed release of single medications and of standardized dosage forms. Transdermal medication devices are not commonly used for dispensing multiple medications, nor for administering personalized medication regimes.

What is needed is apparatus for transdermal drug delivery that may be utilized in an institutional setting, and additionally may be used by ambulatory patients in chronic administration of medications. Another goal is to provide systems for transdermal drug delivery that are simple to use and maintain. A further goal is to provide improved transdermal medication devices capable of administering multiple medications and varied dosage amounts. Another goal is to provide improved transdermal medication devices capable of monitoring administration of medications and providing status information to the patient and to caregivers.

SUMMARY

Disclosed herein are systems and devices for transdermal drug delivery that are comfortable for the patient, mechanically strong, and simple to use. Transdermal drug delivery devices of the disclosure may be worn by a patient or other user as a wristband, armband, or other wearable band. In various embodiments, the transdermal drug delivery devices can be used by ambulatory users and by patients in a hospital or other institutional setting.

A wearable band transdermal medication device includes one or more chambers for dispensing transdermal medication, and a device housing that is configured to receive each of the one or more chambers. The device houses a transdermal applicator for the transdermal medication. The chamber includes a pouch containing a liquid transdermal medication pressurized at a first pressure. In an embodiment, the pouch is formed of a flexible hermetic material that is impervious to the liquid medication. The pouch includes an outlet having an inner surface within the pouch and an outer surface adjacent a fluid volume within a delivery section of the transdermal medication delivery device.

In various embodiments, transdermal medications may include one or more of a therapeutic agent, a nutritional agent, a bioactive agent, and a diagnostic agent. In the present disclosure, transdermal medications are also called transdermal dosage formulations, pharmaceutically active agents, or simply active agents. Additionally, in the present disclosure, transdermal medications are sometimes called liquid medications, or liquid transdermal medications.

The device further includes a controller for controlling dispensing of the liquid transdermal medication from the pouch to the fluid volume within the delivery section of the device. The controller includes an inactive state in which the transdermal medication remains sealed in the pouch of the chamber, and an active state in which the transdermal medication is dispensed through the outlet to the fluid volume.

In an embodiment, the transdermal applicator includes a surface configured to contact skin of a patient at an outer face of the device housing. In an embodiment, the transdermal applicator includes a transfer layer in fluid communication with the fluid volume within the delivery portion, and an adhesive layer at the surface of the transdermal applicator configured to contact skin of a patient at an outer face of the device housing.

In an embodiment, the outlet of the pouch is sealed against dispensing of the liquid medication when a second pressure of the fluid volume within the delivery section is substantially at atmospheric pressure. The outlet dispenses the liquid transdermal medication from the pouch to the fluid volume when the second pressure of the fluid volume is below a negative pressure differential relative to the first pressure within the chamber. In an embodiment, the outlet is a perforated, self-sealing membrane.

In an embodiment, the outlet of the pouch is sealed against dispensing of the transdermal medication when a magnetic valve assembly is in a closed configuration. The outlet is configured to dispense the transdermal medication from the pouch to a fluid volume within a delivery section of the device when the magnetic valve assembly is in an open configuration. In an embodiment, the magnetic valve assembly includes a valve body with a first valve port, and a valve slide with a second valve port. An electromagnet displaces the valve slide to align the second valve port with the first valve port to move the magnetic valve assembly to the open configuration.

In an embodiment, a transdermal medication delivery device comprises a chamber, comprising a pouch containing a transdermal medication, wherein the transdermal medication is a liquid pressurized at a first pressure, said pouch formed of a flexible material that is impervious to the transdermal medication, and including an outlet having an inner surface within the pouch and an outer surface adjacent a fluid volume within a delivery section of the transdermal medication delivery device, wherein the outlet is configured to be sealed against dispensing of the transdermal medication when a second pressure of the fluid volume within the delivery section is substantially at atmospheric pressure, and the outlet is configured to dispense the transdermal medication from the pouch to the fluid volume when the second pressure of the fluid volume is below a negative pressure differential; a transdermal applicator for the transdermal medication; a device housing comprising the delivery portion including the fluid volume adjacent the outer surface of the outlet, a storage portion including a receptacle configured to receive the chamber, and a connector adjacent the delivery portion and the storage portion for connecting to the outlet in an airtight seal; wherein the device housing engages the transdermal applicator in fluid communication with the fluid volume within the delivery portion, and wherein the transdermal applicator includes a surface configured to contact skin of a user at an outer face of the device housing; and a controller for controlling the second pressure of the fluid volume within the delivery portion, the controller including an inactive state in which the second pressure of the fluid volume is substantially at atmospheric pressure and an active state in which the second pressure of the fluid volume is below the negative pressure differential.

In an embodiment, a transdermal medication delivery device comprises a chamber, comprising a pouch containing a transdermal medication, wherein the transdermal medication is a liquid pressurized at a first pressure, said pouch formed of a flexible material that is impervious to the transdermal medication, and including an outlet having an inner surface within the pouch, wherein the outlet is configured to be sealed against dispensing of the transdermal medication when a magnetic valve assembly is in a closed configuration, and is configured to dispense the transdermal medication from the pouch to a fluid volume within a delivery section of the transdermal medication delivery device when the magnetic valve assembly is in an open configuration; a transdermal applicator for the transdermal medication; a device housing comprising the delivery portion including the fluid volume adjacent the outer surface of the outlet, a storage portion including a receptacle configured to receive the chamber, and the magnetic valve assembly; wherein the device housing engages the transdermal applicator in fluid communication with the fluid volume within the delivery portion, and wherein the transdermal applicator includes a surface configured to contact skin of a user at an outer face of the device housing; and a controller for controlling the configuration of the magnetic valve assembly, the controller including an inactive state in which the magnetic valve assembly is in the closed configuration and an active state in which the magnetic valve assembly is in the open configuration.

In an embodiment, a transdermal medication delivery device, comprises a chamber, comprising a pouch containing a transdermal medication, wherein the transdermal medication is a liquid pressurized at a first pressure above atmospheric pressure, said pouch formed of a flexible hermetic material that is impervious to the transdermal medication, and including an outlet having an inner surface within the pouch and an outer surface adjacent a fluid volume within a delivery section of the transdermal medication delivery device, wherein the outlet is configured to be sealed against dispensing of the transdermal medication when a second pressure of the fluid volume within the delivery section is substantially at atmospheric pressure, and the outlet is configured to dispense the transdermal medication from the pouch to the fluid volume when the second pressure of the fluid volume is below a negative pressure differential, the chamber further comprising a pressure sensor for measuring the first pressure; a transdermal applicator for the transdermal medication; a device housing comprising the delivery portion including the fluid volume adjacent the outer surface of the outlet, a storage portion including a receptacle configured to receive the chamber, and a connector adjacent the delivery portion and the storage portion for connecting to the outlet in an airtight seal; wherein the device housing engages the transdermal applicator in fluid communication with the fluid volume within the delivery portion, and wherein the transdermal applicator includes a surface configured to contact skin of a user at an outer face of the device housing; and a controller for controlling the second pressure of the fluid volume within the delivery portion, the controller including an inactive state in which the second pressure of the fluid volume is substantially at atmospheric pressure and an active state in which the second pressure of the fluid volume is below the negative pressure differential, wherein the controller is in electrical communication with the pressure sensor and calculates a medication fill level for the chamber based upon the first pressure measured by the pressure sensor.

Other objects, features, and advantages of the present disclosure will become apparent with reference to the drawings and detailed description of the illustrative embodiments that follow.

BRIEF DESCRIPTION OF THE DRAWINGS

Non-limiting embodiments of the present disclosure are described by way of example with reference to the accompanying figures which are schematic and are not intended to be drawn to scale. Unless indicated as representing the background art, the figures represent aspects of the disclosure.

FIG. 3 is a perspective view of a wearable band transdermal device, showing a chamber aligned with a receptacle of the device, according to an embodiment.

FIG. 4 is a partially schematic cross-sectional view in the plane A-A of a wearable band transdermal device with an inserted chamber, according to the embodiment of FIG. 3.

DETAILED DESCRIPTION

Figure 1:
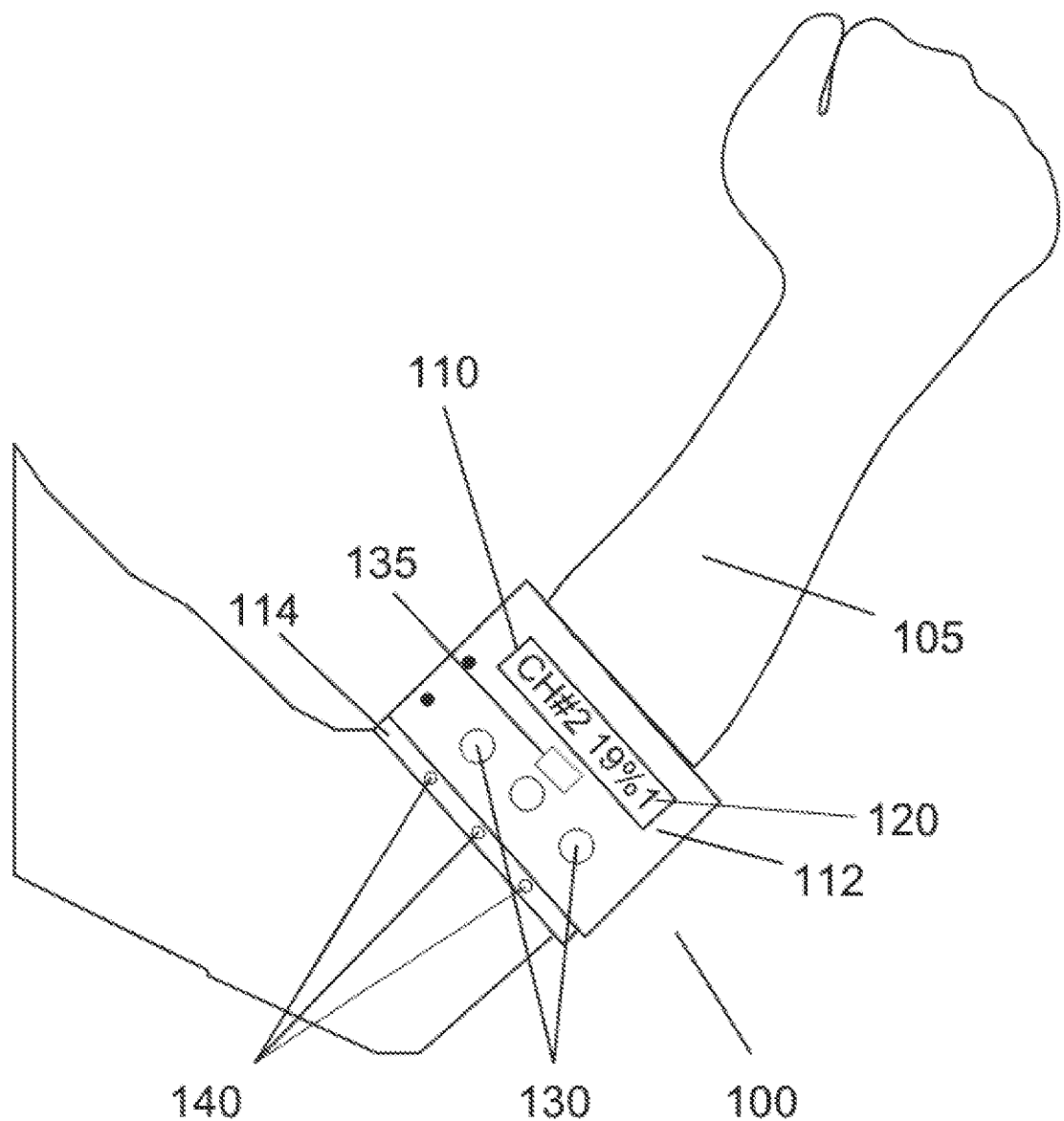
FIG. 1 is a perspective view of a wearable band transdermal device worn by a patient as an armband, according to an embodiment.

In the following detailed description, reference is made to the accompanying drawings, which depict non-limiting, illustrative embodiments of the present disclosure. Other embodiments may be utilized and logical variations, e.g., structural and/or mechanical, may be implemented without departing from the scope of the present disclosure. To avoid unnecessary detail, certain information, items, or details known to those skilled in the art may be omitted from the following description.

A wearable band transdermal medication device includes one or more chamber for dispensing transdermal medication, a device housing that is configured to receive each of the one or more chambers, and a transdermal applicator for the transdermal medication. In the present disclosure, the one or more chambers are sometimes called cartridges. A chamber includes a pouch containing a liquid transdermal medication pressurized at a first pressure. In an embodiment, the pouch is formed of a flexible hermetic material that is impervious to the liquid medication. The pouch includes an outlet having an inner surface within the pouch and an outer surface adjacent a fluid volume within a delivery section of the transdermal medication delivery device.

As used herein, liquid transdermal medications may include a therapeutic agent, a nutritional agent, or other bioactive agent. Additionally, liquid transdermal medications may include diagnostic agents.

In one embodiment, the outlet of the pouch is sealed against dispensing of the liquid medication when a second pressure of the fluid volume within the delivery section is substantially at atmospheric pressure. The outlet dispenses the liquid transdermal medication from the pouch to the fluid volume when the second pressure of the fluid volume is below a negative pressure differential. In an embodiment, outlet is a perforated self-sealing membrane. In an embodiment, the outlet is an elastomeric, thermoplastic, or other material that is configured as a self-sealing membrane that provides an airtight seal when the membrane is not in an activated, open configuration. In various embodiments, the outlet mechanism provides a one-way flow of liquid transdermal medication, preventing flow of transdermal medication back into the pouch.

In another embodiment, the outlet of the pouch is sealed against dispensing of the transdermal medication when a magnetic valve assembly is in a closed configuration. The outlet is configured to dispense the transdermal medication from the pouch to a fluid volume within a delivery section of the transdermal medication delivery device when the magnetic valve assembly is in an open configuration. In an embodiment, the magnetic valve assembly includes a valve body with a first valve port, and a valve slide with a second valve port. An electromagnet displaces the valve slide to align the second valve port with the first valve port to move the magnetic valve assembly to the open configuration.

The device housing incorporates a delivery portion including the fluid volume adjacent the outer surface of the outlet, and a storage portion including one or more receptacles configured to receive respective of the one or more chambers. In an embodiment, the device housing further includes a connector for connecting to the outlet in an airtight seal when a chamber is inserted into a receptacle. In an embodiment, the connector is adjacent the delivery portion and the storage portion of the device housing. In an embodiment, each of one or more chambers includes a rigid tubular shell or case containing the pouch, and one or more receptacles within the device housing. In an embodiment, each receptacle is a slot that extends from an access port at a side of the device housing. In various embodiments, the cartridge may take the form of a tube, e.g., similar to a bullet. The cartridge may have a substantially circular cylindrical cross section, or may have a flattened cylindrical cross section with a circular segment removed, defining a flat surface that carries or adjoins the transdermal applicator, among other possibilities.

In an embodiment, the device housing engages the transdermal applicator in fluid communication with the fluid volume within the delivery portion. The transdermal applicator includes a surface configured to contact skin of a patient at an outer face of the device housing. In an embodiment, the transdermal applicator includes a transfer layer in fluid communication with the fluid volume within the delivery portion, and an adhesive layer at the surface of the transdermal applicator configured to contact skin of a patient at an outer face of the device housing.

The wearable band transdermal medication delivery device further includes a band controller (also herein sometimes simply called a controller) for controlling dispensing of the liquid transdermal medication from the pouch. The controller includes an inactive state in which the transdermal medication remains sealed in the pouch of the chamber, and an active state in which the transdermal medication is dispensed through the outlet to the fluid volume within the delivery section of the transdermal medication delivery device. In embodiments in which the transdermal medication delivery device includes a plurality of chambers, the band controller separately controls dispensing of transdermal medication from each of the chambers.

In an embodiment, the band controller controls a second pressure of the fluid volume within the delivery portion. The controller includes an inactive state in which the second pressure of the fluid volume is substantially at atmospheric pressure, and an active state in which the second pressure of the fluid volume is below a negative pressure differential. In an embodiment, the fluid volume is an air space, and the second pressure is a negative air pressure differential relative to the first pressure of the liquid transdermal medication within the pouch. In an embodiment, the device housing houses a suction pump for regulating the second pressure of the fluid volume within the delivery portion, under electrical control by the controller.

In another embodiment, the band controller controls the configuration of a magnetic valve assembly. The controller includes an inactive state in which the magnetic valve assembly is in a closed configuration, and an active state in which the magnetic valve assembly is in an open configuration. In an embodiment, the controller actuates an electromagnet that displaces a valve slide relative to a valve body of the magnetic valve assembly, to move the magnetic valve assembly between the closed configuration and the open configuration.

In an embodiment, a flexible pouch within the chamber is filled with liquid transdermal medication, with substantially no air within the pouch. In an embodiment, the liquid transdermal medication within the flexible pouch is pressurized at a first pressure above atmospheric pressure. In an embodiment, the pouch includes a first pressure sensor for measuring the first pressure above atmospheric pressure of the liquid transdermal medication, wherein the first pressure sensor is in electrical communication with the band controller. As liquid transdermal medication is dispensed from the flexible pouch, the pouch shrinks to contain the remaining volume of medication, and the first pressure within the pouch decreases. In an embodiment, the band controller determines a medication fill level for liquid transdermal medication within the chamber based upon the sensor readings communicated by the first pressure sensor to the band controller. In an embodiment, when the medication fill level falls below a given threshold, the device provides an alert to the patient, e.g., a visual, audio, and/or vibratory signal. For example, the device 100 of FIG. 1 displays a medication fill level below 20%.

In an embodiment, the wearable band transdermal device further includes a duct that is configured to be housed within the delivery portion of the device. In an embodiment, the duct is interconnected between the outer surface of the outlet and the transdermal applicator, and defines a passage for fluid communication of the transdermal medication during dispensing. In various embodiments, a portion of the duct defines the fluid volume within the delivery section. In various embodiments, a chamber may include a single outlet or multiple outlets, and the wearable band transdermal device may include a single duct or multiple ducts.

In various embodiments, the chamber is designed as a single-use device for dispensing transdermal medication to a given patient. In an embodiment, the chamber is manufactured to store and dispense transdermal medication under aseptic conditions. For example, the pouch may be manufactured and sterilized under conditions suited for the materials of the pouch. The sterile pouch may be aseptically filled with liquid medication that has been pre-sterilized, or alternately, the liquid medication may be sterilized by sterile filtration at the point of filling, and the pouch then sealed.

In an embodiment, the single-use chamber includes other components in the fluid communication path of liquid medication during dispensing of the liquid medication from the pouch within the chamber. In an embodiment, the transdermal applicator is integral with or attached to the chamber. In an embodiment, the chamber further includes a duct integral with or attached to the chamber that is configured to be housed within the delivery portion, and that defines a passage for the fluid communication of the liquid medication during dispensing. In this embodiment, the duct is integral with or attached to the device housing and is configured to fit within the delivery portion of the device housing when the chamber is received within the device housing. In an embodiment, the other components of the single-use chamber that are in the fluid communication path of dispensed liquid medication are sterilized during manufacture of the chamber to avoid contamination of the liquid medication during dispensing.

In an embodiment, non-volatile memory within the chamber stores a transdermal device identifier in electrical communication with the band controller. The transdermal device identifier may include, for example, one or more of a personal identifier for the patient, and an active agent identifier for the liquid medication contained in the pouch. In an embodiment, the transdermal device identifier uniquely identifies a given patient that is authorized to receive the liquid medication within the chamber, and the band controller prevents dispensing of the transdermal medication unless the patient wearing the wearable band transdermal device is authenticated as the authorized patient, e.g., by entering credentials into the wearable band transdermal device. In an embodiment, the transdermal device identifier identifies a pharmaceutically active agent of the transdermal medication within the chamber, and the band controller prevents dispensing of the transdermal medication unless the patient wearing the wearable band transdermal device is authorized to receive that medication.

In one embodiment, a chamber contains transdermal medication that is administered to the patient continuously from a starting time to an ending time, or until a time of depletion of the transdermal medication. In another embodiment, the transdermal medication is administered in multiple bolus doses, dispensed at different points in time. In a further embodiment, the chamber contains a single-dose quantity of the transdermal medication. In various embodiments, the band controller stores medication regimen information, which is used to control timing and quantity of transdermal medication dispensed from one or more chamber of the wearable band transdermal device. In various embodiments, the device contains a set of customized doses of different transdermal medications, scheduled for release at different times during a day or at different times over a period of several days, in accordance with a prescription or set of prescriptions for a given patient. Customized dosing information can ensure dosing sufficient for symptom relief, while avoiding overdoses.

In an embodiment, the wearable band transdermal device is configured to be worn by an ambulatory individual who requires long-term medications but who is not hospitalized. In another embodiment, the wearable band transdermal device is worn by a patient in an hospital or other healthcare institution, where it may be used for administering transdermal medication under supervision of healthcare providers.

FIG. 1 is a perspective view of a wearable band transdermal device 100 in the form of an armband worn on the patient's arm 105, according to an embodiment. The wearable band transdermal device is configured to conformably contact and cover a body region either in part or whole, and may worn by a user at various target locations of the user's body. In various embodiments, the wearable band transdermal device may be worn at the user's wrist (e.g., bracelet), arm (e.g., armband), leg (e.g., leg band), torso (e.g., waist band), or head (e.g., headband).

The armband transdermal device 100 includes a device housing 110, which may be formed of an engineering plastic or other sturdy, lightweight material. In an embodiment, armband transdermal device 100 is strong and impact resistant, and can be safely and securely used during fitness activities and sports. The upper face 112 of housing 110 includes various control and display components of device 100. A display 120 may provide a visual output such as an LCD display or other visual display, an audio output such as a speaker, or other outputs such as vibratory signals. Input devices 130 may include, e.g., a keypad, a touch sensitive pad, a track ball, a motion detecting device, and a microphone, among others. Power switch 135 may turn on and off supply of power to electrical components of the armband transdermal device 100 from a battery or other power source 640 (FIG. 11), or may control supply of power to selected electrical components while other components receive continuous power regardless of the state of power switch 135.

Side face 114 of housing 110 contains three access ports 140 for access to receptacles for insertion and removal of chambers or cartridges containing liquid medication (not shown in this view). Device housing also includes a lower or outer surface facing the skin of the patient, which surface presents one or more transdermal applicator (not shown in this view) for transdermal administration of medication to the patient.

Figure 2:
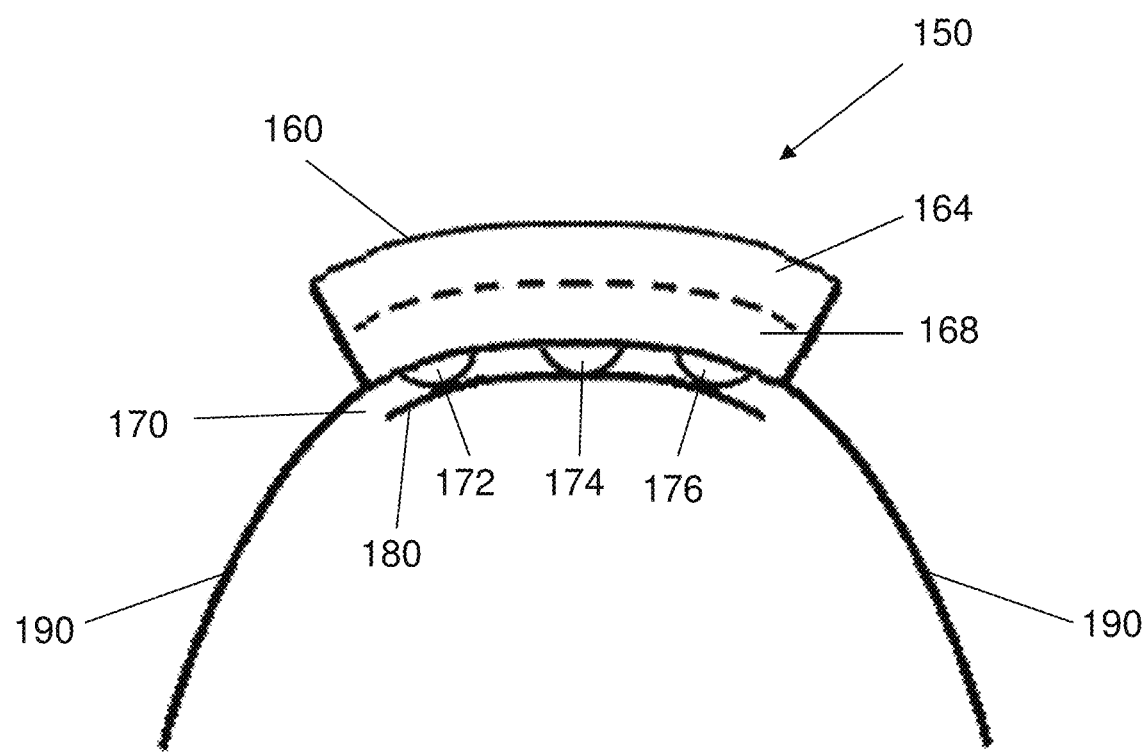
FIG. 2 is a schematic sectional view of a wearable band transdermal device, according to an embodiment.

As seen in the schematic sectional view of FIG. 2, a device housing 160 of a wearable band transdermal device 150 may be contoured, e.g., outwardly convex, to fit comfortably to an arm or other body part of the patient. Wearable band transdermal device 150 includes a storage portion 164 configured to receive and store chambers or cartridges containing liquid medications. Wearable band transdermal device 150 also includes a dispensing portion 168 configured to deliver liquid medications dispensed from chambers contained in the storage portion 164 for transdermal medication to the patient via one or more transdermal applicators housed in the device. The wearable band transdermal device 150 further includes fasteners 180 such as buckles or Velcro® hook and loop fabric strips (Velcro is a registered trademark of Velcro S.A. Corporation, Lenzerheide, Grisons Switzerland), to secure the device to an arm or other body part of a patient.

Three transdermal applicator members 172, 174, 176 protrude from the dispensing portion 168, and a transdermal applicator sheet 180 is located below these applicator members. Transdermal applicator sheet 180 contacts the patient's skin, and transfers liquid medication received from the transdermal applicator members 172, 174, 176.

The storage portion 164 of the device housing may be positioned above the delivery portion 168 as shown in this view, or may be positioned in another spatial arrangement, such as a side-by-side arrangement (FIG. 4). In various embodiments, the delivery portion of the device housing is positioned between the transdermal applicator and one or more outlet of the storage portion, and defines or contains one or more passages for fluid communication of transdermal medication from the outlet to the transdermal applicator.

FIG. 3 is a perspective view of a wearable band transdermal device 200, showing a cartridge 220 aligned with a receptacle of the device for insertion. A device housing 210 includes a storage section 214, which contains a three receptacles 216, also herein called slots, for receiving and storing cartridges 220 (in FIG. 3 one of the receptacles 216 is shown, in phantom). The wearable band transdermal device 210 of FIG. 3 houses up to three cartridges, but a wearable band transdermal device may be configured to house more, or fewer, cartridges depending on size and capacity of the cartridges and size of the device. In an embodiment, a wearable band transdermal device has a capacity to hold sufficient cartridges to administer chronic transdermal medications over a desired period of time, e.g., days or weeks. In an embodiment, transdermal medications within device 210 may be updated when cartridges are spent or discontinued, simply by removing and replacing the cartridges. Multiple cartridges within device 210 may contain the same, or different, transdermal medications. Multiple cartridges may be controlled to dispense transdermal medications at the same, or different, times.

Access ports 218 provide access to the slots 216 for insertion of cartridges. Optionally, access ports 218 may include doors or covers (not shown here) to close the slots when not being used to insert or remove cartridges. The device 210 may include mechanisms (not shown) to lock cartridges within receptacles 210, and may include mechanisms to control insertion or removal of cartridges, such as a mechanism to eject a cartridge. Device housing 210 also includes a delivery portion 250, here shown at the left end of the housing 210.

Cartridge or chamber 220 stores liquid medication for controlled dispensing by the wearable band transdermal device 200. Cartridge 220 includes a pouch 224 contained within a cartridge housing 222 (also herein called a shell or case). In an embodiment, the pouch is formed of a flexible, hermetic material, while the shell 222 is formed of a rigid material that is impervious to liquid medication. Pouch 226 contains liquid medication 226. In an embodiment, pouch 224 is substantially completely filled with liquid medication, and contains little or no air. In an embodiment, the liquid medication 226 is pressurized within pouch 224 at higher than atmospheric pressure. Cartridge 220 includes an outlet 230 at one end of the cartridge. In an embodiment, the outlet 230 comprises a membrane 232 including a perforation 234. In an embodiment, the membrane is a self-sealing membrane in which the perforation 234 is normally sealed, in the absence of a physical mechanism for opening the perforation. When the cartridge is fully inserted in slot 216, the outlet 230 is coupled to a connector 252 at the end of the slot. In an embodiment, connector 252 is located adjacent the storage portion 214 and the delivery portion 250 of device housing 210. In an embodiment, connector 252 cooperates with outlet 230 in dispensing medication from chamber 220.

Figure 5:
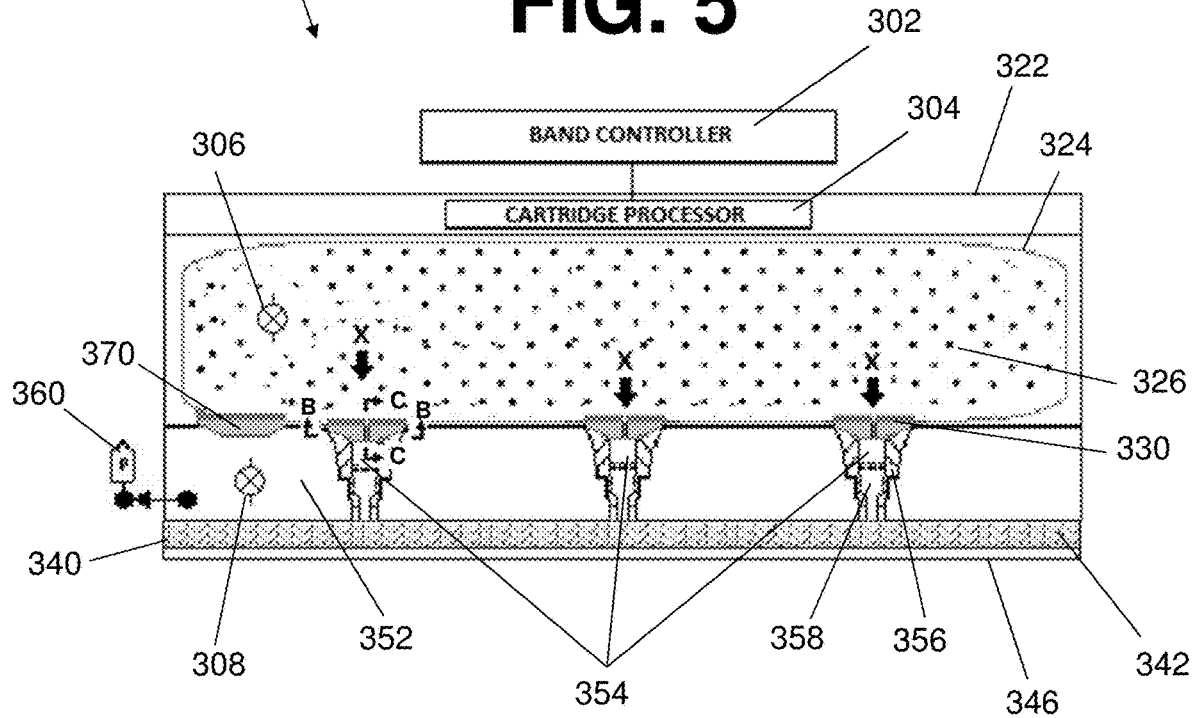
FIG. 5 is a partially schematic sectional diagram of a chamber for a wearable band transdermal device, according to an embodiment.
Figure 10:
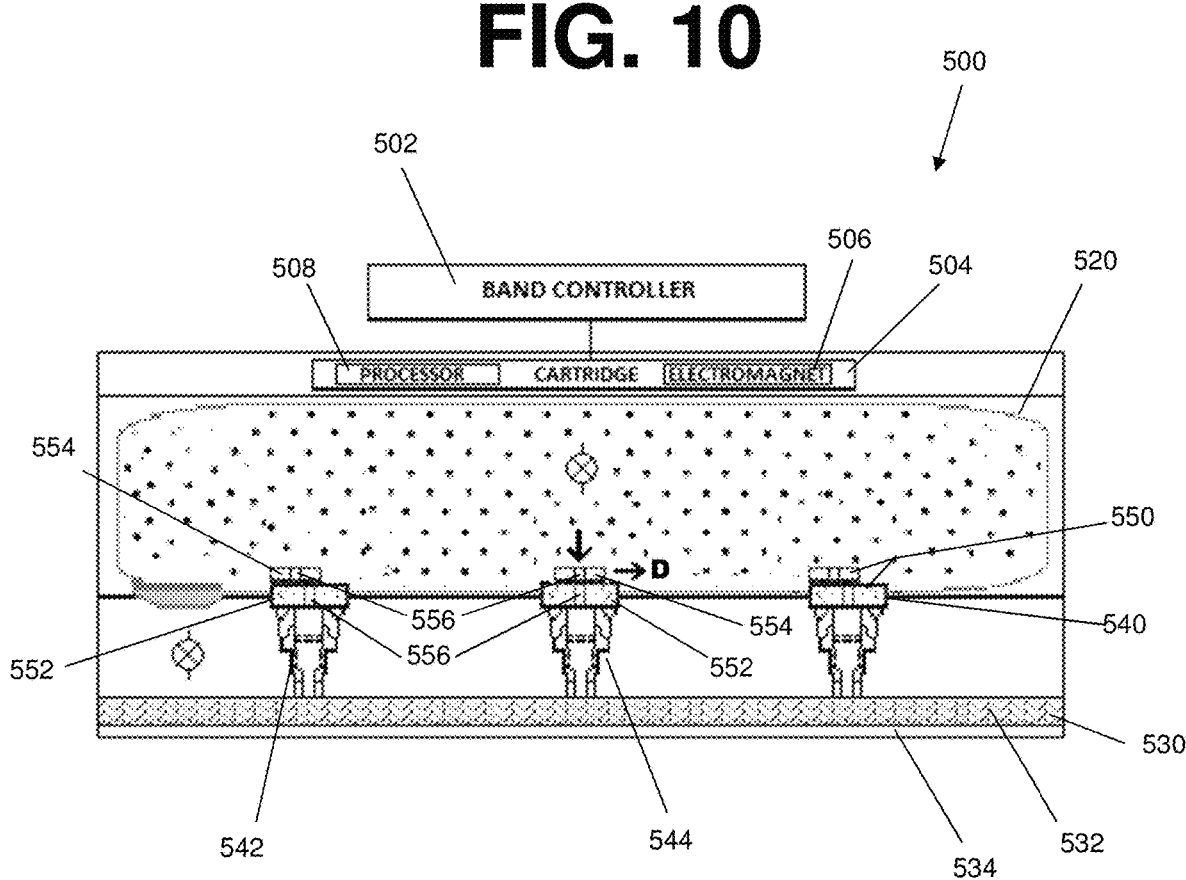
FIG. 10 is a partially schematic sectional diagram of a chamber for a wearable band transdermal device, according to an embodiment.

FIG. 4 is a partial cross-sectional view of a cartridge 220 inserted in one of the slots of wearable band transdermal device 200, in a section at the plane A-A in FIG. 3. Device 200 includes a transdermal applicator 240, which is an applicator pad or strip at the bottom of cartridge 220. At one end of device housing 210, delivery portion 250 includes a fluid volume 254 (e.g., an air space) adjacent an exterior surface of outlet 230. Delivery portion 250 also includes a passage, here shown schematically by arrow 258, for fluidic communication of liquid medication dispensed from cartridge 220 to the transdermal applicator 240. In an embodiment, the delivery chamber 250 includes a duct (e.g., as shown in FIGS. 5, 10) that defines the passage 258.

Cartridge 220 includes a cartridge processor 242 in electrical communication with a band processor 244 of device 200. These processors may communicate with each other via wired and/or wireless communications, such as electrical communication via cartridge electrical connector 246 and band electrical connector 248. In an embodiment, when cartridge 220 is inserted into slot 216 (arrow E), cartridge processor 242 communicates data stored by the cartridge to band processor 244.

In an embodiment, band processor 244 controls operation of a negative pressure pump 260 contained within device housing 210. Negative pressure pump 260 is also called a suction pump in this disclosure, and is here shown schematically. When suction pump 260 creates sufficient negative pressure differential between the pressure within the fluid volume 254 and the pressure of liquid medication 226 within pouch 224, liquid medication is drawn from pouch 224 through an opened perforation 234 of membrane 232 and flows to transdermal applicator pad 240 for administration to a patient wearing device 200. When suction pump 260 is inactivated, fluid volume 254 reverts to atmospheric pressure and self-sealing membrane 232 reseals, stopping dispensing of liquid medication from cartridge 220. In an embodiment, suction pump communicates with a valve manifold (not shown), to independently control pressure within separate fluid volumes 254 respectively associated with the three cartridges within device 210, thereby to activate dispensing of medication only from one, or two, of the three cartridges at a given time. In an embodiment, a wearable band transdermal device incorporates multiple small suction pumps to control dispensing of medication from respective cartridges.

In an embodiment, the medications to be dispensed by the wearable band transdermal device of the disclosure are stored within the device in liquid form. A liquid composition may comprise, for example, a solution, suspension or emulsion formulation of a compound or pharmaceutically acceptable salt in a suitable liquid carrier(s), for example, ethanol, glycerin, sorbitol, non-aqueous solvent such as polyethylene glycol, oils or water, with a suspending agent, preservative, surfactant, wetting agent, or coloring agent.

In some embodiments, the physical state of liquid transdermal medication may change when it is dispensed to the fluid volume in the delivery section of the device housing. For example, the dispensed transdermal medication may take the form of particles dispersed in air or gas within the fluid volume. It should be understood that references herein to liquid medication refer to the state of the transdermal medication within the chamber, and not necessarily to the state of the transdermal medication after dispensing from the chamber.

In some embodiments, the transdermal medication formulation includes an inactive component, e.g., carrier and/or excipient. In an embodiment, a given transdermal medication is a pharmaceutically active agent in pure form. In another embodiment, a given transdermal medication is a pharmaceutically active agent formulated with an excipient. In various embodiments, an excipient is formulated in conjunction with the pharmaceutically active agent for properties such as long-term stabilization, or for conferring a therapeutic enhancement on the active ingredient in the final dosage form, such as facilitating drug absorption, reducing viscosity, or enhancing solubility. In some embodiments, transdermal medication formulations are formulated to control release of the drug by facilitating transport of the drug across the skin (stratum corneum). In various embodiments, excipients may be employed for bulking up formulations that contain potent active ingredients (e.g., bulking agents, fillers, or diluents).

In various embodiments, transdermal dosage formulations have physiochemical and pharmacokinetic properties suitable for transdermal administration. With regard to physiochemical properties, lipophilicity and molecular size are significant determinants of stratum corneum permeability (dermal absorption). Lipophilicity can be a key feature of drug acceptance by the stratum corneum. In an embodiment, transdermally administered drugs have log octanol-water partition in the range 0.8-3.3. Highly polar or charged substances generally are not accepted by the stratum corneum. Drug diffusivity, in general, is size dependent, i.e., large molecules diffuse more slowly than small molecules. As for interaction between these properties, it has been observed that small polar compounds often have higher permeabilities than expected because of the importance of high diffusivity. Desirably, the drug molecule should have adequate solubility in both lipophilic and aqueous environments. These characteristics enable the drug molecule to cross the stratum corneum, a lipoidal barrier; and then transfer to viable epidermis and upper dermis, which are much more aqueous in nature. In various embodiments, in administering a therapeutic agent or other bioactive agent, the wearable band transdermal delivery device may provide systemic administration, or may provide local administration of the therapeutic agent or other bioactive agent.

Wearable band transdermal drug delivery systems of the present disclosure can administer a wide range of therapeutic agents. Examples include analgesics such as opioid (fentanyl and buprenorphine) and nonsteroidal anti-inflammatory drugs (NSAIDs) (diclofenac); antihypertensive drugs such as nitroglycerin (NTG); anticholinergics such as scopolamine; and other pharmaceutically active agents such as clonidine, rivastigmine, selegiline MAOI, methylphenidate, cyanocobalamin, nicotine, etc.

Additionally, the transdermal drug delivery systems can administer nutritional aids. Examples include minerals and metals, vitamins, amino acids, coenzymes, antioxidants, steroids, and hormones. Minerals and metals include boron, calcium, magnesium, chromium, selenium, zinc, etc. Vitamins include Vitamin A (Retinoids), Vitamin B1 (Thiamine), Vitamin B2 (Riboflavin), Vitamin B3 (Niacin), Vitamin B5 (Pantothenic acid), Vitamin B6 (Pyridoxine), Vitamin B7 (Biotin), Vitamin B9 (Folic acid), Vitamin B12 (Cyanocobalamin), Vitamin C (Ascorbic acid), Vitamin D2-D4 (Lumisterol, Ergocalciferol, Cholecalciferol, Dihydrotachysterol, 7-Dehydrocholesterol), Vitamin E (Tocopherol, Tocotrienol), etc. Amino acids include Isoleucine, Alanine, Leucine, Asparagine, Lysine, Aspartate, Methionine, Cysteine, Phenylalanine, Glutamate, Threonine, Glutamine, Tryptophan, Glycine, Valine, Proline, Arginine, Serine, Histidine and Tyrosine, etc. Coenzymes include Coenzyme A, Coenzyme B12, Coenzyme Q, NAD, FAD, ATP, molybdopterin, etc. Antioxidants include Glutathione, Lutein, alpha-lipoic acid, polyphenols, Grape seed extract, superoxide dismutase, epicathechin, proanthocyanidins, sulfoxides, etc.

Common categories of steroids and steroid precursors are anabolic steroids; corticosteroids, which include glucocorticoids and mineralocorticoids; and sex steroids. Anabolic steroids interact with androgen receptors to increase muscle and bone synthesis. Glucocorticoids regulate aspects of metabolism and immune function, and are often prescribed reduce inflammatory conditions like asthma and arthritis. Mineralocorticoids help maintain blood volume and control renal excretion of electrolytes. Sex steroids are a subset of sex hormones that produce sex differences or support reproduction, and include androgens, estrogens, and progestagens. Examples of hormones include estrogen and testosterone.

An example of treatment application via transdermal administration of therapeutic agents is fatigue management, which may include dosing regimes for stimulants as well as reducing the need for a follow-up depressant to induce sleep. Another exemplary treatment application is treatment of diabetes to maintain blood glucose levels at close to normal. In an exemplary embodiment, antihyperglycemic drugs are administered via transdermal delivery to control noninsulin-dependent diabetes mellitus (NIDDM). Another exemplary treatment application is hormone replacement therapy, which seeks to restore youthful levels of hormones that decline with age (e.g., growth hormone, testosterone, estrogen, progesterone, melatonin, DHEA and thyroid). A further exemplary treatment application is obesity and weight management, in which treatments such as low-fat diet and regular exercise can be enhanced via controlled use of appetite suppressants.

An exemplary category of diagnostic applications is transdermal administration of radioactive tracers to measure rates of glucose uptake and other metabolic processes. In an exemplary application, a glucose clamp administers radiotracer labeled glucose via transdermal delivery to measure how well a patient metabolizes glucose.

Figure 6:
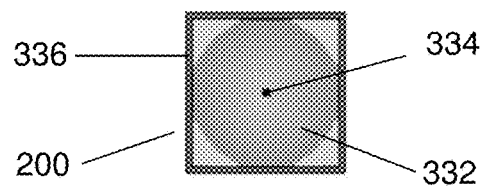
FIG. 6 is a section in the plane B-B of an outlet of the chamber for a wearable band transdermal device, according to the embodiment of FIG. 5.
Figure 7:
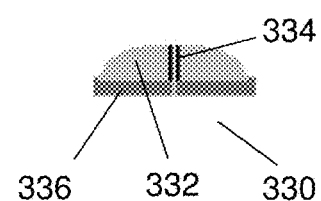
FIG. 7 is a section in the plane C-C of an outlet of the chamber for a wearable band transdermal device, according to the embodiment of FIG. 5.

FIG. 5 is a partially schematic sectional diagram of a cartridge 300 for a wearable band transdermal device. Cartridge 300 includes a shell, case, or cartridge housing 322 that houses a flexible pouch 324 containing liquid medication 326. Cartridge 300 includes three outlets 330 that control dispensing (indicated by arrows X) of liquid medication to fluid volumes 354 defined by ducts 356 extending from exterior surface of the outlets 330. In various embodiments, the ducts may be pipes, tubes, conduits, spouts, or other members defining passages between outlets 330 and transdermal applicator 240. As seen in the sectional view of FIG. 6 taken at the plane B-B in FIG. 5, a given outlet 330 includes a membrane 332 with a central perforation 334, the membrane being sealed at its periphery by a gasket 336. As seen in the sectional view of FIG. 7 taken at the plane C-C in FIG. 5, the membrane is a truncated hemispherical structure 334, and self-sealing perforation 334 extends from an inner outlet surface of membrane 334 adjacent gasket 336 to an outer outlet surface at the top of this view. The inner surface of each of membranes 332 is positioned within pouch 324, while the outer outlet surface of each of membranes 332 is adjacent the fluid volumes 354 defined by ducts 356.

Cartridge 300 further includes a cartridge processor 304 in electrical communication with a band controller 302 of a wearable transdermal band device containing this cartridge. Pouch 324 includes a first pressure sensor 306 that monitors a first pressure of liquid medication 326 within pouch 326. In an embodiment, the first pressure sensor communicates first pressure sensor readings wirelessly to the cartridge processor 304 and/or to the band processor 302. In an embodiment, the first pressure is above atmospheric pressure. Cartridge 300 also includes a second pressure 308 that monitors a second pressure within a fluid volume 354 within one or more of the ducts 356. In one embodiment, a single second pressure sensor 308 measures a common second pressure of all three fluid volumes 354. In another embodiment, separate pressure sensors monitor pressures within the respective fluid volumes 354.

Pressure sensors 306, 308 may include various types of pressure sensor, such as absolute pressure sensors, which measure pressures relative to perfect vacuum; gauge pressure sensors, which measure pressure relative to atmospheric pressure; and vacuum pressure sensors, which measure pressures below atmospheric pressure. In various embodiments, vacuum pressure sensors may indicate the difference between that low pressure and atmospheric pressure (i.e., negative gauge pressure), or they may indicate below atmospheric pressure relative to perfect vacuum (i.e., absolute pressure). In an embodiment, outputs of pressure sensors 306, 308 are processed to determine a negative pressure differential between the second pressure within fluid volume(s) 354 and the first pressure within pouch 324.

In an embodiment, in an active state of band controller 302, the band controller activates suction pump 360. Suction pump 360 creates sufficient negative pressure differential between the second pressure within the fluid volumes 354 and the first pressure of liquid medication 326 within pouch 234 to cause liquid medication 326 to be dispensed through outlets 330. The liquid medication is drawn from pouch 324 through opened perforations 334 of membranes 332, and flows to transdermal applicator 340 for administration to a patient. Ducts 356 define passages 358 for fluidic communication of liquid medication from fluid volumes 354 to transdermal applicator 340. When suction pump 360 is inactivated, fluid volumes 354 revert to atmospheric pressure and self-sealing membranes 332 reseal, stopping dispensing of liquid medication from cartridge 300.

In an embodiment, the transdermal applicator 340 is in contact with stratum corneum layer of patient's skin (not shown). The stratum corneum is an epidermal layer of skin. When the cartridge 300 is activated, fluid medication is dispensed to the transport layer 342, then flows through an adhesive layer 346 to the skin (e.g., stratum corneum) of a patient.

In certain embodiments, the transport layer 342 controls a rate of transport of transdermal medication to adhesive layer 346 following initial release of the medication from pouch 324. In some embodiments, transport layer 342 may also control diffusion of transdermal medication across the plane of the transdermal applicator 340 relative to discrete locations at which the ducts 356 transfer the medication to the transport layer 342. In some embodiments, the transport layer is a polymeric membrane that controls a rate of transport of transdermal medication dispensed from cartridge 300. In some embodiments, the rate of transfer of a drug through the transport layer 342 is slower than the rate of medication diffusion across the stratum corneum. In other embodiments, the transdermal applicator includes multiple transport layers. In an embodiment, the adhesive layer 346 is a pressure-sensitive adhesive, which may be a solvent-free, permanently tacky, viscoelastic adhesive capable of adhering to a patient's skin without causing undue discomfort. In various embodiments, pressure-sensitive adhesive 346 may be an acrylate, silicone, or rubber based adhesive.

Cartridge 300 further includes a manual pump 370 for actuating dispensing of liquid medication from pouch 324. Manual pump 370 serves as a backup mechanism for dispensing transdermal medication in the event electrically controlled suction pump 360 becomes inoperable. In the illustrated embodiment, manual pump 370 includes a bulb squeezable by hand, which compresses a flow of liquid medication from pouch 324 when squeezed. In an embodiment, flow of liquid medication is prevented by a check valve (not shown) when the bulb is enlarged to its unsqueezed configuration. In an embodiment, the check valve is in fluid communication with one of ducts 356 or with another passage to deliver manually dispensed transdermal medication to the transdermal applicator 340.

Figure 8:
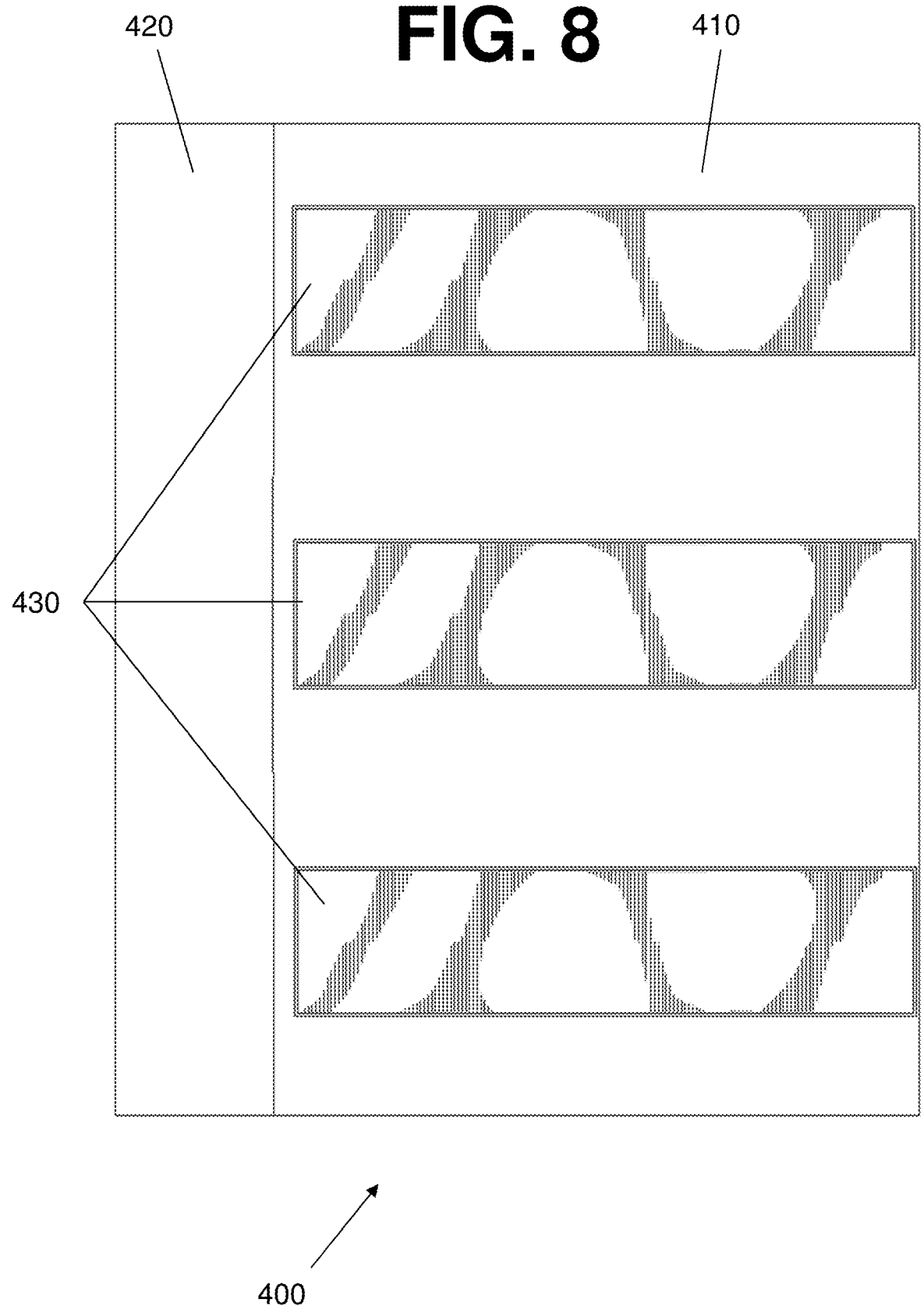
FIG. 8 is a bottom plan view of a wearable band transdermal device with a plurality of transdermal applicator strips, according to an embodiment.

FIG. 8 shows a plan view of the bottom or outer surface of a wearable band transdermal device housing 400 facing a patient's skin. Device housing 400 includes a source portion 410 and a delivery portion 420. The source portion includes three transdermal applicator strips 420, respectively associated with three chambers (not shown) within device housing 430. This arrangement provides separate application of transdermal medications dispensed from the respective cartridges, without intermingling of the medications.

Figure 9:
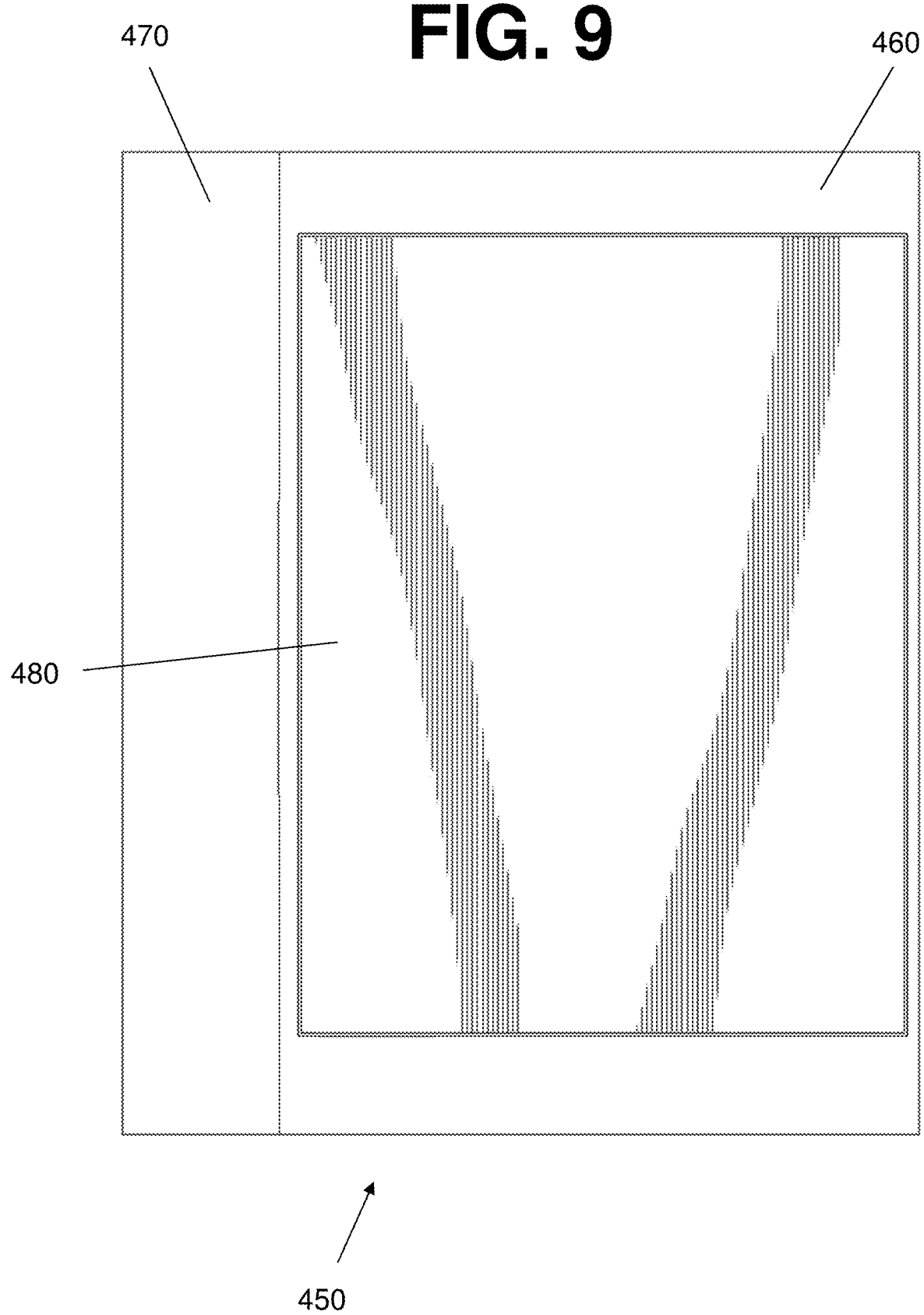
FIG. 9 is a bottom plan view of a wearable band transdermal device with a transdermal applicator sheet, according to an embodiment.

FIG. 9 shows a plan view of the bottom or outer surface of a further wearable band transdermal device housing 450 facing a patient's skin. Device housing 450 includes a source portion 460 and a delivery portion 470. The source portion includes a single transdermal applicator sheet 480, which may be associated with one or more chambers (not shown) within device housing 450. This arrangement provides a broader area of application of transdermal medications dispensed from wearable band applicator device, although in certain cases it may result in intermingling medications dispensed by multiple chambers.

FIG. 10 is a partially schematic sectional diagram of a cartridge 500 for a wearable band transdermal device, according to an embodiment. Many components of cartridge 500 correspond to components of the cartridge 300 of FIG. 5, and reference should be had to the discussion of FIG. 5 for a description of these components. Cartridge 500 differs from cartridge 300 in the mechanism of outlets 540 in dispensing liquid medication from pouch 520. Outlets 540 include magnetic valve assemblies 550 that prevent dispensing of the liquid medication when the magnetic valve assemblies are in a closed configuration. The magnetic valve assemblies are configured to dispense the liquid medication from the pouch 520 to fluid volumes 542 when the magnetic valve assemblies in an open configuration.

Magnetic valve assemblies include magnetic valve bodies 552 with respective valve body ports 556, and magnetic valve slides 554 with respective valve slide ports 558. As shown in the central magnetic valve assembly 550, the magnetic valve assembly is moved to its open configuration by displacing the magnetic valve slide 554 as shown at arrow D, thereby aligning the valve slide port 558 with the valve body port 556 to permit dispensing of liquid medication through the magnetic valve assembly. The cartridge controller 504 selectively actuates one or more electromagnet 506, which exerts magnetic force to displace the magnetic valve slides 554 between their closed configuration and their open configuration.

Figure 11:
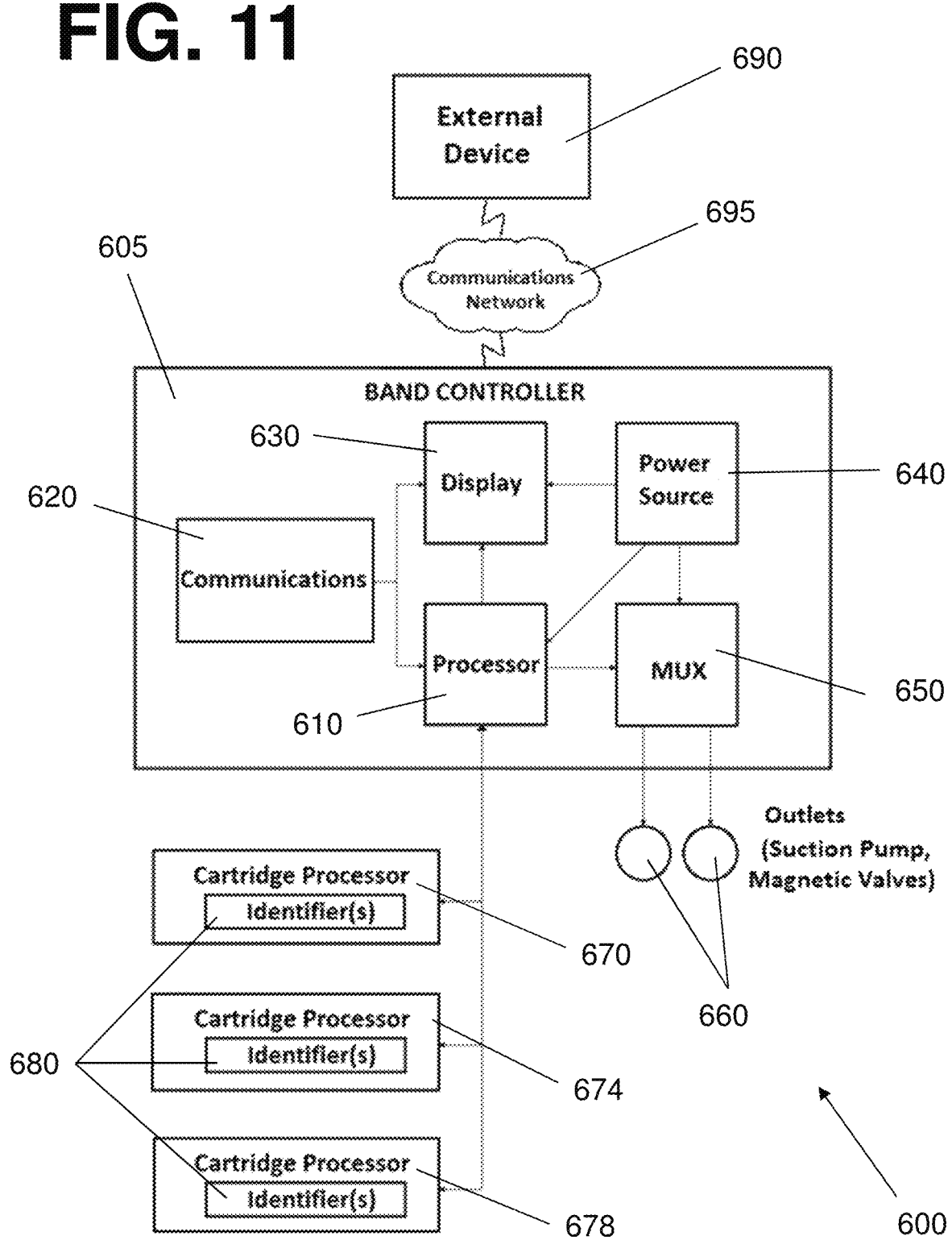
FIG. 11 is a block schematic diagram of a control system for a wearable band transdermal device, according to an embodiment.

FIG. 11 is a block schematic diagram of a control system 600 for a wearable band transdermal device (not shown). The control system 600 includes a band controller 605 for the wearable band transdermal device, and three cartridge processors 670, 674, 678 respectively associated with three chambers (not shown) stored within the wearable band transdermal device. The band controller 605 for transdermal medication device 300 includes a communications interface 620, a processor 610, a display 630, a multiplexer (MUX 650), and a power source 640. The power source provides energy for actuating outlets (e.g., suction pump or magnetic valves) respectively associated with one or more given chamber(s) housed in the device; here, two outlets are shown. The display 630 may provide a visual output such as an LCD display, an audio output such as sound from a speaker, and other outputs such as vibratory signals. In various embodiments, band processor 610 is programmed to actuate dispensing of transdermal medication from respective chambers of the device at pre-selected times, in a selected sequence, or in some other programmed arrangement. In an embodiment, processor 610 directs power, e.g., electrical current, from power source 640 to actuating mechanisms associated with given outlets 660 through multiplexer circuit (MUX) 650.

In various aspects, the communications interface 620 may comprise one or more interfaces such as, for example, a wireless communications interface, a network interface, a transmit interface, a receive interface, a media interface, a system interface, a component interface, a switching interface, a chip interface, a microprocessor, and so forth. When implemented by a wireless device or within wireless system, for example, the mobile computer may include a wireless interface comprising one or more antennas, transmitters, receivers, transceivers, amplifiers, filters, control logic, etc.

In various implementations, the described aspects may communicate over wireless shared media in accordance with a number of wireless protocols. Examples of wireless protocols may include various wireless local area network (WLAN) protocols, including the Institute of Electrical and Electronics Engineers (IEEE) 802.xx series of protocols, such as IEEE 802.11a/b/g/n, IEEE 802.16, IEEE 802.20, etc. Other examples of wireless protocols may include various wireless wide area network (WWAN) protocols, such as GSM cellular radiotelephone system protocols with GPRS, CDMA cellular radiotelephone communication systems with 1×RTT, EDGE systems, EV-DO systems, EV-DV systems, HSDPA systems, and so forth. Further examples of wireless protocols may include wireless personal area network (PAN) protocols, such as an Infrared protocol, a protocol from the Bluetooth Special Interest Group (SIG) series of protocols, including Bluetooth Specification versions v1.0, v1.1, v1.2, v2.0, v2.0 with Enhanced Data Rate (EDR), as well as one or more Bluetooth Profiles, and so forth. Yet another example of wireless protocols may include near-field communication techniques and protocols, such as electro-magnetic induction (EMI) techniques. An example of EMI techniques may include passive or active radio-frequency identification (RFID) protocols and devices. Other suitable protocols may include Ultra Wide Band (UWB), Digital Office (DO), Digital Home, Trusted Platform Module (TPM), ZigBee, etc.

Wireless communication modes of communications interface 620 may include any mode of communication between points that utilizes, at least in part, wireless technology including various protocols and combinations of protocols associated with wireless transmission, data, and devices. The points include, for example, wireless devices such as wireless headsets, audio and multimedia devices and equipment, such as audio players and multimedia players, telephones, including mobile telephones and cordless telephones, and computers and computer-related devices and components, such as printers.

In an embodiment, band controller 605 communicates with one or more external device 690 via communication network 695. Communications network 695 may employ various modes of communications such as wireless communications, wired communications, and combinations of the same. In an exemplary embodiment, external device 695 is a pharmacy computer system that communicates electronic prescription data to the wearable band transdermal device when filling a prescription with a chamber. In another embodiment, a pharmacy computer system adjusts dosing of transdermal medication dependent based upon laboratory blood tests of the patient, and communicates updated electronic prescription data to the wearable band transdermal device over the Internet. In a further embodiment, external device 695 is a radio frequency identification patient wristband worn by the patient wearing the wearable band transdermal device. The RFID patient wristband communicates patient identification data in order to authenticate the patient to receive transdermal medication. In yet another embodiment, external device 695 is a healthcare management system at a healthcare provider institution (e.g., hospital, hospice, or resident care center) that communicates with the wearable band transdermal device for in-patient administration of transdermal medications. In an exemplary communication with the healthcare management system 695, band controller 605 uploads historical data on dispensing of transdermal medications. In an exemplary communication with the healthcare management system 695, the band controller 605 downloads updated physician instructions (regimen) for dispensing of transdermal medications.

Band controller 605 communicates with cartridge processors 670, 674, 678 respectively associated with three chambers of a wearable band transdermal device. In an embodiment, non-volatile memory within each of the cartridge processors stores one or more transdermal device identifier(s) 680. Transdermal device identifier(s) 680 are communicated to band processor 610 and may be processed to authorize dispensing of transdermal medications.

In an embodiment, the transdermal device identifier 680 includes a personal identifier associating a chamber with a given patient or other subject. This personal identifier can associate the ingestible medication device with a personal identification number for a given patient, such as an official number used for tracking individuals like a social security number or driver's license number, or a patient identification number that can be assigned by a healthcare provider institution, among other possibilities. In authenticating dispensing of transdermal medication using a personal identifier, the system 100 can act upon credentials entered into the wearable band transdermal device by the patient wearing the device, or can act upon other sources such as a personal identifier contained in an RFID patient wristband worn by the patient.

In certain embodiments, the transdermal device identifiers 680 includes active agent identifier(s), i.e., data identifying a pharmaceutically active agent of the transdermal medication stored in the chamber. In an embodiment, an active agent identifier identifies a particular active agent selected from a group or plurality of different pharmaceutically active agents. In certain embodiments the active agent identifier may, when associated with a batch of chambers containing the identical pharmaceutically active agent, be indistinguishable from an active agent identifier for any other chamber of the batch. In yet other embodiments, the active agent identifier uniquely identifies a given chamber, even from other chambers containing the identical pharmaceutically active agent. In certain embodiments, the transdermal device identifier 680 generates a unique signal that distinguishes a given unit dosage from other unit dosages of a defined population of unit dosages, e.g., a prescription, a batch or a lifetime production run of transdermal medications.

In various embodiments, the control system 600 may analyze additional data besides patient identifiers and active agent identifiers to determine whether to actuate outlet(s) to dispense transdermal medication. For example, the analysis can include data concerning medication regimen, drug allergies, or patient medical history. This additional data may be stored in cartridge processors 670, 674, 678 and/or in band controller 605.

In an exemplary embodiment, a transdermal device identifier 680 uniquely identifies a given patient that is authorized to receive the liquid medication within the chamber, and band processor 610 prevents dispensing 660 of the transdermal medication unless the patient wearing the wearable band transdermal device is authenticated as the authorized patient by wirelessly reading a personal identifier on an RFID hospital wristband worn by the patient. In an exemplary embodiment, a transdermal device identifier 680 identifies a pharmaceutically active agent of a transdermal medication within the chamber, and band processor 610 prevents dispensing 660 of the transdermal medication if the patient wearing the wearable band transdermal device is allergic to the pharmaceutically active agent.

While various aspects and embodiments have been disclosed, other aspects and embodiments are contemplated. The various aspects and embodiments disclosed are for purposes of illustration and are not intended to be limiting, with the true scope and spirit being indicated by the following claims.

The foregoing method descriptions and the interface configuration are provided merely as illustrative examples and are not intended to require or imply that the steps of the various embodiments must be performed in the order presented. As will be appreciated by one of skill in the art the steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed here may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

What is claimed is:

1. A transdermal medication delivery device, comprising:
a chamber comprising a pouch containing a transdermal medication, wherein the transdermal medication is a liquid pressurized at a first pressure, said pouch formed of a flexible material that is impervious to the transdermal medication, and including an outlet having an inner surface within the pouch and an outer surface adjacent a fluid volume within a delivery section of the transdermal medication delivery device, wherein the chamber is configured to not dispense the transdermal medication from the pouch to the fluid volume when a second pressure of the fluid volume within the delivery section is substantially at atmospheric pressure, and the chamber is configured to dispense the transdermal medication from the pouch to the fluid volume when the second pressure of the fluid volume is below a negative pressure differential;
a transdermal applicator for the transdermal medication;
a device housing comprising the delivery section including the fluid volume adjacent the outer surface of the outlet, a storage portion including a receptacle configured to receive the chamber, and a connector adjacent the delivery portion and the storage portion for connecting to the outlet in an airtight seal; wherein the device housing engages the transdermal applicator in fluid communication with the fluid volume within the delivery section, and wherein the transdermal applicator includes a surface configured to contact skin of a user at an outer face of the device housing; and
a controller for controlling the second pressure of the fluid volume within the delivery section, the controller including an inactive state in which the second pressure of the fluid volume is substantially at atmospheric pressure and an active state in which the second pressure of the fluid volume is below the negative pressure differential.

2. The device of claim 1 further comprising a suction pump for regulating the second pressure of the fluid volume within the delivery section, wherein the suction pump operates under electrical control by the controller.

3. The device of claim 1, wherein the transdermal applicator for the transdermal medication comprises a transfer layer in fluid communication with the fluid volume within the delivery section, and an adhesive layer at the surface of the transdermal applicator configured to contact skin of a user at an outer surface of the device housing.

4. The device of claim 1, wherein the transdermal applicator is integral with or attached to the chamber.

5. The device of claim 1, within the first pressure is above atmospheric pressure, wherein the chamber further includes a first pressure sensor for measuring the first pressure, and the first pressure sensor is in electrical communication with the controller.

6. The device of claim 5, wherein the controller calculates a medication fill level for the chamber based upon the first pressure measured by the first pressure sensor.

7. The device of claim 1, further comprising a second pressure sensor for measuring the second pressure, wherein the second pressure sensor is in electrical communication with the controller.

8. The device of claim 1, wherein the fluid volume is a volume of air, and the second pressure is an air pressure of the volume of air.

9. The device of claim 1, wherein the chamber comprises a tubular shell containing the pouch, and the receptacle comprises a tubular slot extending from an access port in a side of the device housing.

10. The device of claim 1, wherein the transdermal medication delivery device comprises a plurality of chambers, and wherein the device housing includes a plurality of receptacles configured to receive respective ones of the plurality of chambers.

11. The device of claim 1, further comprising non-volatile memory within the chamber that stores a transdermal device identifier in electrical communication with the controller, the transdermal device identifier comprising one or more of a personal identifier for the user, and an active agent identifier for the transdermal medication contained in the chamber.

12. The device of claim 1, further comprising a duct within the delivery section interconnected between the outer surface of the outlet and the transdermal applicator.

13. The device of claim 1, wherein the fluid volume comprises a plurality of fluid volumes within the delivery section of the transdermal medication delivery device, wherein the chamber comprises a plurality of outlets each having an inner surface within the pouch and an outer surface adjacent a respective fluid volume of the plurality of fluid volumes, wherein the a controller for controlling the second pressure of the fluid volume within the delivery section independently controls a respective second pressure of each of the plurality of fluid volumes.

14. A transdermal medication delivery device, comprising:
a chamber comprising a pouch containing a transdermal medication, wherein the transdermal medication is a liquid pressurized at a first pressure above atmospheric pressure, said pouch formed of a flexible hermetic material that is impervious to the transdermal medication, and including an outlet having an inner surface within the pouch and an outer surface adjacent a fluid volume within a delivery section of the transdermal medication delivery device, wherein the chamber is configured to not dispense the transdermal medication from the pouch to the fluid volume when a second pressure of the fluid volume within the delivery section is substantially at atmospheric pressure, and the chamber is configured to dispense the transdermal medication from the pouch to the fluid volume when the second pressure of the fluid volume is below a negative pressure differential, the chamber further comprising a pressure sensor for measuring the first pressure;
a transdermal applicator for the transdermal medication;
a device housing comprising the delivery section including the fluid volume adjacent the outer surface of the outlet, a storage portion including a receptacle configured to receive the chamber, and a connector adjacent the delivery section and the storage portion for connecting to the outlet in an airtight seal; wherein the device housing engages the transdermal applicator in fluid communication with the fluid volume within the delivery section, and wherein the transdermal applicator includes a surface configured to contact skin of a user at an outer face of the device housing; and
a controller for controlling the second pressure of the fluid volume within the delivery section, the controller including an inactive state in which the second pressure of the fluid volume is substantially at atmospheric pressure and an active state in which the second pressure of the fluid volume is below the negative pressure differential, wherein the controller is in electrical communication with the pressure sensor and calculates a medication fill level for the chamber based upon the first pressure measured by the pressure sensor.

* * * * *